United States Patent
Salter et al.

(10) Patent No.: US 9,583,968 B2
(45) Date of Patent: Feb. 28, 2017

(54) PHOTOLUMINESCENT DISINFECTING AND CHARGING BIN

(71) Applicant: Ford Global Technologies, LLC, Dearborn, MI (US)

(72) Inventors: Stuart C. Salter, White Lake, MI (US); James Hadley Muiter, Plymouth, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 299 days.

(21) Appl. No.: 14/518,378

(22) Filed: Oct. 20, 2014

(65) Prior Publication Data

US 2015/0137747 A1 May 21, 2015

Related U.S. Application Data

(63) Continuation-in-part of application No. 14/301,635, filed on Jun. 11, 2014, which is a continuation-in-part of application No. 14/156,869, filed on Jan. 16, 2014, now Pat. No. 9,440,583, which is a continuation-in-part of application No. 14/086,442, filed on Nov. 21, 2013.

(51) Int. Cl.
*B60Q 1/00* (2006.01)
*B60Q 1/26* (2006.01)
*H02J 7/02* (2016.01)
*A61L 2/10* (2006.01)
*B60N 3/14* (2006.01)
*H02J 7/00* (2006.01)

(52) U.S. Cl.
CPC .............. *H02J 7/025* (2013.01); *A61L 2/10* (2013.01); *B60N 3/14* (2013.01); *H02J 7/0047* (2013.01)

(58) Field of Classification Search
CPC .... A61L 2/10; B60N 3/00; B60N 3/14; B60Q 3/00; B60Q 3/008; B60Q 3/02; B60Q 3/022; B60Q 3/0243; H02J 7/0047; H02J 7/025
USPC ................... 362/487–488, 509–510
See application file for complete search history.

(56) References Cited

U.S. PATENT DOCUMENTS

| | | | |
|---|---|---|---|
| 5,709,453 | A | 1/1998 | Krent et al. |
| 6,031,511 | A | 2/2000 | DeLuca et al. |
| 6,117,362 | A | 9/2000 | Yen et al. |
| 6,490,351 | B1 | 12/2002 | Roberts |

(Continued)

FOREIGN PATENT DOCUMENTS

| | | |
|---|---|---|
| CN | 2685145 Y | 3/2005 |
| CN | 201169230 Y | 12/2008 |

(Continued)

OTHER PUBLICATIONS https://www.phonesoap.com/product/phonesoap-charger/.

*Primary Examiner* — Jason Moon Han
(74) *Attorney, Agent, or Firm* — Vichit Chea; Price Heneveld LLP

(57) ABSTRACT

A charging and disinfecting tray for a vehicle is disclosed. The charging and disinfecting tray comprises a wireless charger for charging an electronic device and a lighting apparatus. The lighting apparatus comprises a disinfecting apparatus, which incorporates at least one photoluminescent indicator. A controller is in communication with the wireless charger and the lighting apparatus and is operable to control the photoluminescent indicator by initiating a sterilization operation with the disinfecting apparatus.

20 Claims, 6 Drawing Sheets

(56) References Cited

U.S. PATENT DOCUMENTS

| | | |
|---|---|---|
| 6,494,490 B1 | 12/2002 | Trantoul |
| 6,577,073 B2 | 6/2003 | Shimizu et al. |
| 6,729,738 B2 | 5/2004 | Fuwausa et al. |
| 6,737,964 B2 | 5/2004 | Samman et al. |
| 6,773,129 B2 | 8/2004 | Anderson, Jr. et al. |
| 6,820,888 B1 | 11/2004 | Griffin |
| 6,851,840 B2 | 2/2005 | Ramamurthy et al. |
| 6,859,148 B2 | 2/2005 | Miller |
| 6,871,986 B2 | 3/2005 | Yamanaka et al. |
| 6,953,536 B2 | 10/2005 | Yen et al. |
| 6,990,922 B2 | 1/2006 | Ichikawa et al. |
| 7,161,472 B2 | 1/2007 | Strumolo et al. |
| 7,213,923 B2 | 5/2007 | Liu et al. |
| 7,264,366 B2 | 9/2007 | Hulse |
| 7,264,367 B2 | 9/2007 | Hulse |
| 7,441,914 B2 | 10/2008 | Palmer et al. |
| 7,501,749 B2 | 3/2009 | Takeda et al. |
| 7,575,349 B2 | 8/2009 | Bucher et al. |
| 7,745,818 B2 | 6/2010 | Sofue et al. |
| 7,753,541 B2 | 7/2010 | Chen et al. |
| 7,834,548 B2 | 11/2010 | Jousse et al. |
| 7,862,220 B2 | 1/2011 | Cannon et al. |
| 7,987,030 B2 | 7/2011 | Flores et al. |
| 8,016,465 B2 | 9/2011 | Egerer et al. |
| 8,022,818 B2 | 9/2011 | la Tendresse et al. |
| 8,071,988 B2 | 12/2011 | Lee et al. |
| 8,097,843 B2 | 1/2012 | Agrawal et al. |
| 8,136,425 B2 | 3/2012 | Bostick |
| 8,163,201 B2 | 4/2012 | Agrawal et al. |
| 8,178,852 B2 | 5/2012 | Kingsley et al. |
| 8,197,105 B2 | 6/2012 | Yang |
| 8,203,260 B2 | 6/2012 | Li et al. |
| 8,207,511 B2 | 6/2012 | Bortz et al. |
| 8,232,533 B2 | 7/2012 | Kingsley et al. |
| 8,247,761 B1 | 8/2012 | Agrawal et al. |
| 8,286,378 B2 | 10/2012 | Martin et al. |
| 8,408,766 B2 | 4/2013 | Wilson et al. |
| 8,415,642 B2 | 4/2013 | Kingsley et al. |
| 8,421,811 B2 | 4/2013 | Odland et al. |
| 8,466,438 B2 | 6/2013 | Lambert et al. |
| 8,481,970 B2 | 7/2013 | Cooper et al. |
| 8,519,359 B2 | 8/2013 | Kingsley et al. |
| 8,519,362 B2 | 8/2013 | Labrot et al. |
| 8,552,848 B2 | 10/2013 | Rao et al. |
| 8,606,430 B2 | 12/2013 | Seder et al. |
| 8,624,716 B2 | 1/2014 | Englander |
| 8,631,598 B2 | 1/2014 | Li et al. |
| 8,664,624 B2 | 3/2014 | Kingsley et al. |
| 8,683,722 B1 | 4/2014 | Cowan |
| 8,724,054 B2 | 5/2014 | Jones |
| 8,754,426 B2 | 6/2014 | Marx et al. |
| 8,773,012 B2 | 7/2014 | Ryu et al. |
| 8,846,184 B2 | 9/2014 | Agrawal et al. |
| 8,876,352 B2 | 11/2014 | Robbins et al. |
| 8,952,341 B2 | 2/2015 | Kingsley et al. |
| 9,006,751 B2 | 4/2015 | Kleo et al. |
| 9,057,021 B2 | 6/2015 | Kingsley et al. |
| 9,065,447 B2 | 6/2015 | Buttolo et al. |
| 9,187,034 B2 | 11/2015 | Tarahomi et al. |
| 9,299,887 B2 | 3/2016 | Lowenthal et al. |
| 2002/0159741 A1 | 10/2002 | Graves et al. |
| 2002/0163792 A1 | 11/2002 | Formoso |
| 2003/0179548 A1 | 9/2003 | Becker et al. |
| 2004/0213088 A1 | 10/2004 | Fuwausa |
| 2006/0087826 A1 | 4/2006 | Anderson, Jr. |
| 2006/0097121 A1 | 5/2006 | Fugate |
| 2006/0188389 A1 | 8/2006 | Levy |
| 2007/0032319 A1 | 2/2007 | Tufte |
| 2007/0285938 A1 | 12/2007 | Palmer et al. |
| 2009/0219730 A1 | 9/2009 | Syfert et al. |
| 2009/0251920 A1 | 10/2009 | Kino et al. |
| 2009/0260562 A1 | 10/2009 | Folstad et al. |
| 2009/0262515 A1 | 10/2009 | Lee et al. |
| 2011/0012062 A1 | 1/2011 | Agrawal et al. |
| 2012/0001406 A1 | 1/2012 | Paxton et al. |
| 2012/0104954 A1 | 5/2012 | Huang |
| 2012/0183677 A1 | 7/2012 | Agrawal et al. |
| 2012/0280528 A1 | 11/2012 | Dellock et al. |
| 2013/0335994 A1 | 12/2013 | Mulder et al. |
| 2014/0065442 A1 | 3/2014 | Kingsley et al. |
| 2014/0103258 A1 | 4/2014 | Agrawal et al. |
| 2014/0264396 A1 | 9/2014 | Lowenthal et al. |
| 2014/0266666 A1 | 9/2014 | Habibi |
| 2014/0373898 A1 | 12/2014 | Rogers et al. |
| 2015/0046027 A1 | 2/2015 | Sura et al. |
| 2015/0138789 A1 | 5/2015 | Singer et al. |
| 2015/0267881 A1 | 9/2015 | Salter et al. |
| 2016/0016506 A1 | 1/2016 | Collins et al. |

FOREIGN PATENT DOCUMENTS

| | | |
|---|---|---|
| CN | 101337492 A | 1/2009 |
| CN | 201193011 Y | 2/2009 |
| CN | 201418882 Y | 3/2010 |
| CN | 202207332 U | 5/2012 |
| CN | 103227490 A | 7/2013 |
| CN | 203425270 U | 2/2014 |
| DE | 29708699 U1 | 7/1997 |
| DE | 10319396 A1 | 11/2004 |
| EP | 1793261 A1 | 6/2007 |
| EP | 2778209 A1 | 9/2014 |
| JP | 2000159011 A | 6/2000 |
| JP | 2007238063 A | 9/2007 |
| WO | 2006022466 A1 | 3/2006 |
| WO | 2006047306 A1 | 5/2006 |
| WO | 2014068440 A1 | 5/2014 |

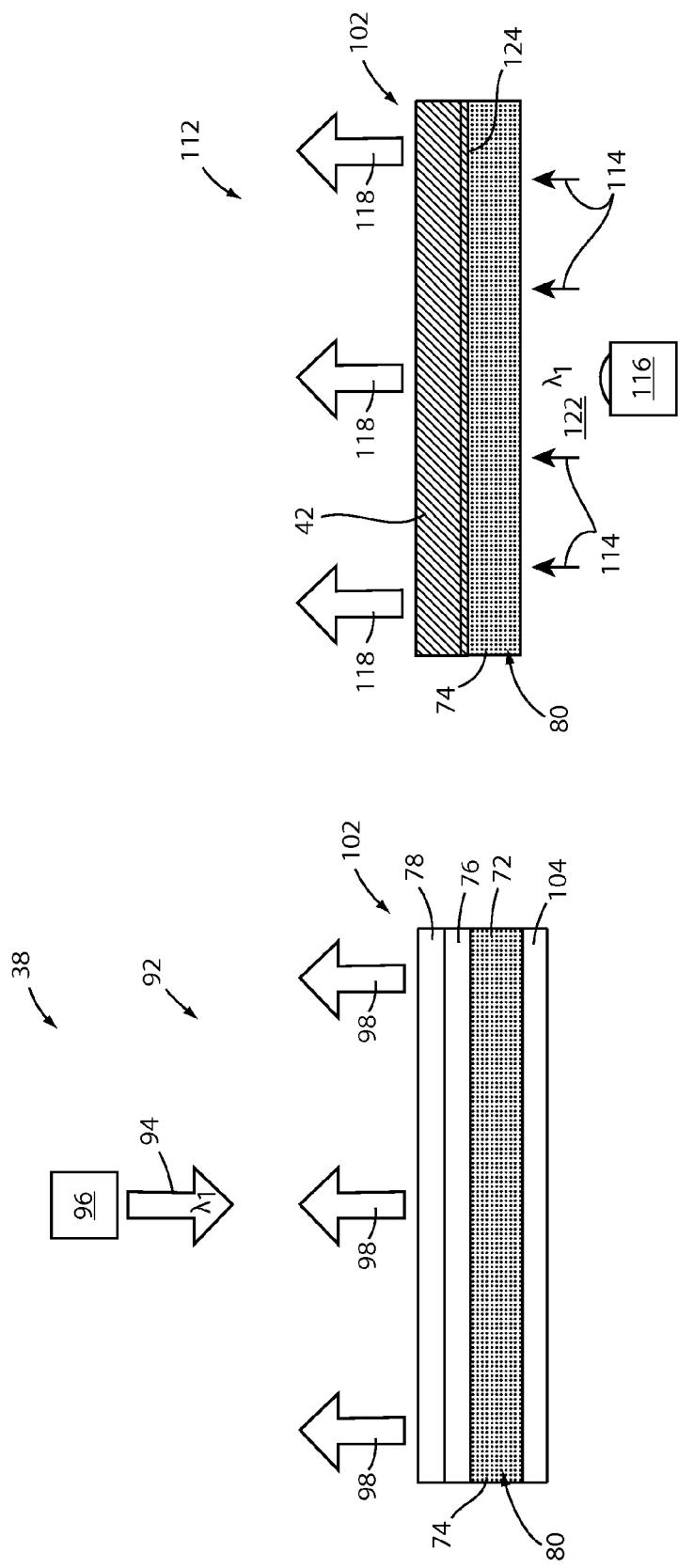

US 9,583,968 B2

PHOTOLUMINESCENT DISINFECTING AND CHARGING BIN

CROSS-REFERENCE TO RELATED APPLICATIONS

This application is a continuation-in-part of U.S. Pat. No. 9,499,096, filed Jun. 11, 2014, and entitled "PHOTOLUMINESCENT VEHICLE READING LAMP," which is a continuation-in-part of U.S. Pat. No. 9,440,583, filed on Jan. 16, 2014, entitled "VEHICLE DOME LIGHTING SYSTEM WITH PHOTOLUMINESCENT STRUCTURE," which is a continuation-in-part of U.S. patent application Ser. No. 14/086,442, filed Nov. 21, 2013, and entitled "VEHICLE LIGHTING SYSTEM WITH PHOTOLUMINESCENT STRUCTURE." The aforementioned related applications are hereby incorporated by reference in their entirety.

FIELD OF THE INVENTION

The present invention generally relates to vehicle charging systems, and more particularly to vehicle charging sterilization systems for electronic devices.

BACKGROUND OF THE INVENTION

Portable electronic devices have become an integral part of daily life. However, recent studies have shown that such devices can transmit infections, which may lead to various illnesses and dermatological issues. The disclosure provides for an illuminated charging bin utilizing photoluminescent materials to generate ambient light to notify a passenger of a status of at least a disinfection status of a device.

SUMMARY OF THE INVENTION

According to one aspect of the present invention, a charging and disinfecting tray for a vehicle is disclosed. The charging and disinfecting tray comprises a wireless charger for charging an electronic device and a lighting apparatus. The lighting apparatus comprises a disinfecting apparatus, which incorporates at least one photoluminescent indicator. A controller is in communication with the wireless charger and the lighting apparatus and is operable to control the photoluminescent indicator by initiating a sterilization operation with the disinfecting apparatus.

According to another aspect of the present invention, a charging apparatus for a vehicle is disclosed. The charging apparatus comprises a wireless charger for charging an electronic device disposed in a compartment and a lighting apparatus comprising at least one photoluminescent indicator. A controller is in communication with the charging apparatus and the lighting apparatus and is configured to output a color of light corresponding to a charge level of the electronic device by controlling the lighting apparatus.

According to yet another aspect of the present invention, a charging and disinfecting tray for a vehicle is disclosed. The charging and disinfecting tray comprises a wireless charger for charging an electronic device and a lighting apparatus, which may include a disinfecting apparatus. The disinfecting apparatus comprises at least one photoluminescent indicator. A controller is configured to control the wireless charger and the lighting apparatus. The controller is operable to activate the photoluminescent indicator by initiating a sterilization operation with the disinfecting apparatus.

These and other aspects, objects, and features of the present invention will be understood and appreciated by those skilled in the art upon studying the following specification, claims, and appended drawings.

BRIEF DESCRIPTION OF THE DRAWINGS

In the drawings:

FIG. 5 is a schematic view of a front-lit configuration of a lighting apparatus configured to convert an excitation emission to an output emission;

FIG. 6 is a schematic view of a back-lit configuration of a lighting apparatus configured to convert an excitation emission to an output emission;

DETAILED DESCRIPTION OF THE PREFERRED EMBODIMENTS

As required, detailed embodiments of the present disclosure are disclosed herein. However, it is to be understood that the disclosed embodiments are merely exemplary of the disclosure that may be embodied in various and alternative forms. The figures are not necessarily to a detailed design and some schematics may be exaggerated or minimized to show function overview. Therefore, specific structural and functional details disclosed herein are not to be interpreted as limiting, but merely as a representative basis for teaching one skilled in the art to variously employ the present disclosure.

As used herein, the term "and/or," when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

Figure 1:
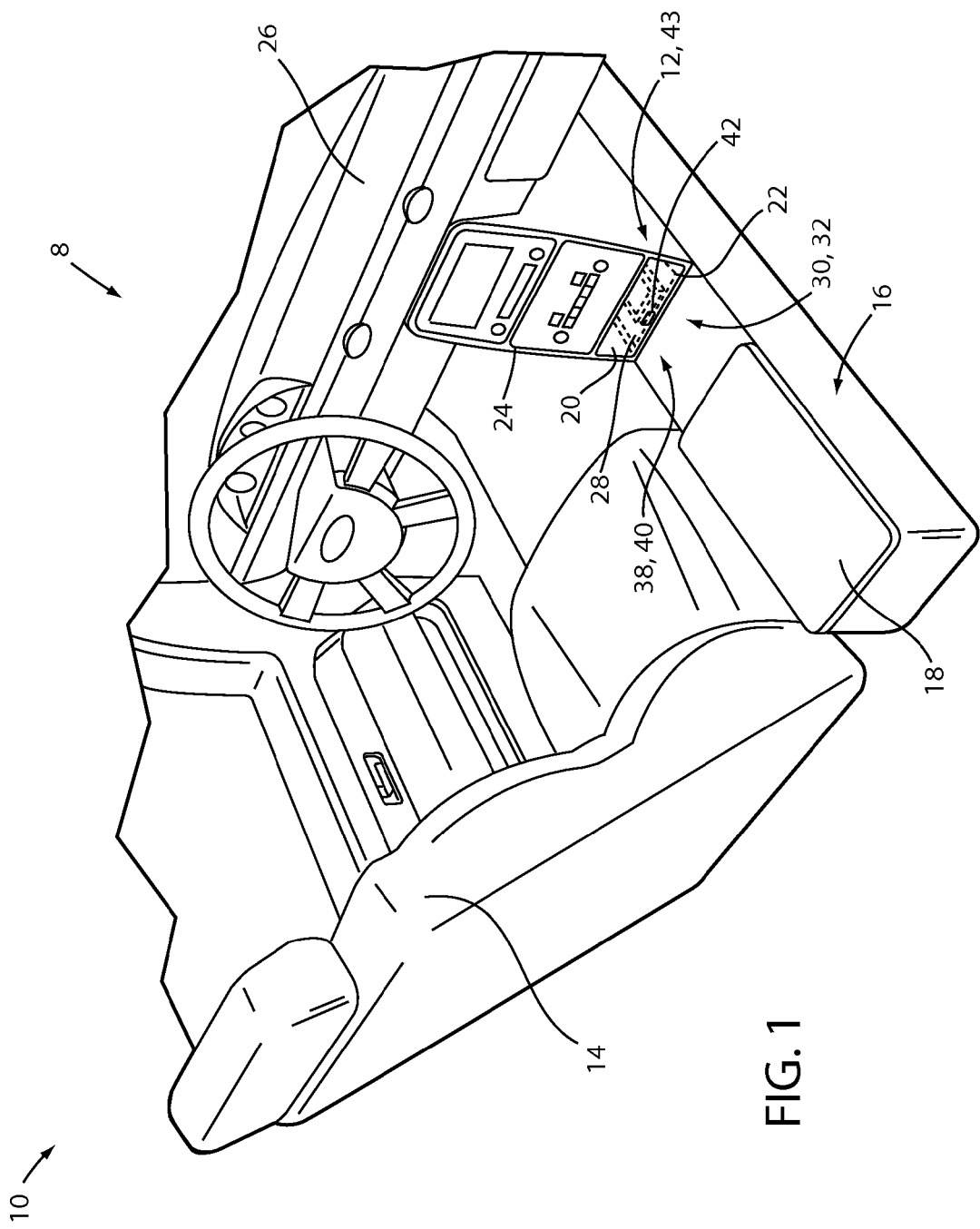
FIG. 1 is a perspective view of a passenger compartment of a vehicle employing a wireless charging and disinfecting system.

Referring to FIG. 1, a passenger compartment 8 of an automotive vehicle 10 is generally illustrated employing a wireless charging and disinfecting system 12. The vehicle 10 generally includes a seating arrangement including a front driver seat 14 adapted to seat a person as an occupant in the passenger compartment 8. The vehicle 10 also includes a center console 16 comprising a storage compartment 18 and a tray 20. The storage compartment 18, the tray 20 and/or various containers or compartments throughout the vehicle 10 may comprise a wireless charging and sterilizing system 22. Hereinafter, the wireless charging and sterilizing system 22 may also be referred to as the system 22.

The center console 16 comprises a center stack 24 extending to a dashboard 25. The vehicle 10 may further be equipped with various other vehicle assemblies, for example, device holders such as trays and storage compartments. Each of the trays, storage compartments, and a variety of other vehicle components may be configured to wirelessly charge and disinfect one or more devices as discussed herein. Such trays and storage compartments may be located in various locations throughout the vehicle. The disclosure provides for a novel wireless charging and sterilizing system 22 that may comprise photoluminescent materials configured to illuminate a storage compartment or tray in which the system is disposed to provide an indication of at least a disinfection status of a device.

A charging region 28 of the system 22 may be located in the tray 20 of the center console 16 and configured to receive an electronic device 26. The system 22 comprises a charging apparatus 30 for wirelessly charging one or more devices, including one or more rechargeable batteries for providing electrical power within an electronic device. In some embodiments, the wireless charging apparatus 30 may correspond to an inductive charging system. It should be appreciated that other forms of wireless transmission may be employed in the wireless charging apparatus 30 such as magnetic resonance, loose coupled resonance and electromagnetic radiation according to other embodiments.

In some embodiments, one or more wireless charging apparatuses 30 may be provided in one or more storage trays or dedicated trays provided in the center console 16. The wireless charging apparatus 30 includes a wireless charger 32, such as inductive charger according to some embodiments. Inductive chargers typically include one or more inductive coils for generating electric signals in the form of an electromagnetic field (EMF) typically at low frequencies (approximately less than 500 kHz) within a charging region 28. In the embodiment shown, the charging region 28 may be defined by a tray or a storage compartment having a bottom wall and side walls for receiving the device 26, such that the device 26, when located within the charging region 28, may be charged via the electromagnetic field through inductive coupling.

The system 22 may further comprise a lighting apparatus 38 comprising a disinfecting apparatus 40 located in the tray 20. The tray may comprise an access door 42 which may be rotatably connected to the tray 20 such that a cavity formed by the tray may be accessed by opening the door 42. The access door 42 and the tray 20 may be formed of a material and/or comprise one or more coatings configured to absorb ultraviolet light utilized to disinfect the device. In some embodiments, the access door 42 and the tray 20 may be of polymeric materials, for example polycarbonate or acrylic, configured to absorb and/or block ultraviolet radiation emitted by the disinfecting apparatus 40. As described herein, the tray 20 and the access door 42 may form a charging and disinfecting compartment 43 configured to house the device 26 and prevent ultraviolet radiation from escaping into the passenger compartment 8.

The lighting apparatus 38 may be configured to illuminate at least one photoluminescent material by utilizing at least one light source configured to emit a first emission of light. The first emission may correspond to light having a wavelength of approximately less than 500 nm. In some embodiments, the lighting apparatus 38 may comprise a plurality of light sources. At least one of the pluralities of light sources may correspond to an ultraviolet light source which may provide for disinfecting capabilities of the disinfecting apparatus 40. The lighting apparatus 38 may further comprise at least one photoluminescent portion configured emit luminous light to identify at least one of a charging status or a disinfecting status of the system 22.

In some embodiments, the lighting apparatus 38 may comprise a first light source and a second light source. The first light source may be configured to emit the first emission and the second light source may be configured to emit a second emission. The first emission may be in the visible light range having a wavelength that may be approximately less than 500 nm and greater than a wavelength from the second emission. The second light source may correspond to the ultraviolet light source and be configured to emit the second emission corresponding to a wavelength in the ultraviolet light range of approximately 10 nm to 400 nm.

The lighting apparatus 38 may comprise a first photoluminescent portion having a first absorption range and a second photoluminescent having a second absorption range. Each of the photoluminescent portions may be disposed proximate an interior cavity of the tray 20 and may be configured to be excited by the first emission and/or the second emission at various intensities to selectively emit one of a plurality of colors of light. In order to provide for the lighting apparatus 38 to selectively generate the plurality of colors the first photoluminescent portion may comprise a first absorption range and the second photoluminescent portion may comprise a second absorption range. The first absorption range may correspond to a first wavelength of the first emission and the second absorption range may correspond to a second wavelength of the second emission.

In this configuration, the first absorption range and the second absorption range may be significantly different having little or no overlap in activation wavelengths corresponding to their respective photoluminescent material structures. As such, the lighting apparatus 38 may illuminate the tray 20 by exciting the first photoluminescent portion and the second photoluminescent portion independently to output a status indicator of the system 22. The first photoluminescent portion and the second photoluminescent portion may be referred to as first photoluminescent indicator and a second photoluminescent indicator, respectively. As discussed in further detail throughout the disclosure, in some embodiments the system 22 may be configured to charge a portable device, disinfect the portable device, and emit a light corresponding to a charging status and/or a disinfecting status.

For clarity, an emission output from the first photoluminescent portion may be referred to as a third emission and an emission output from the second photoluminescent portion may be referred to as a fourth emission. Each of the third emission and the fourth emission may also be referred to as output emissions. Such designations may serve to demonstrate exemplary arrangements and compositions and should not be considered to designate a specific number of elements or essential components of any specific implementation of the disclosure, unless clearly specified otherwise. Further, the specific numeric designations in the specification may not correspond to similar numeric designations in the claims. For example, the terms first, second, third, etc. may refer to an order of introduction of elements in the claims which may differ in order in the specification.

Figure 2:
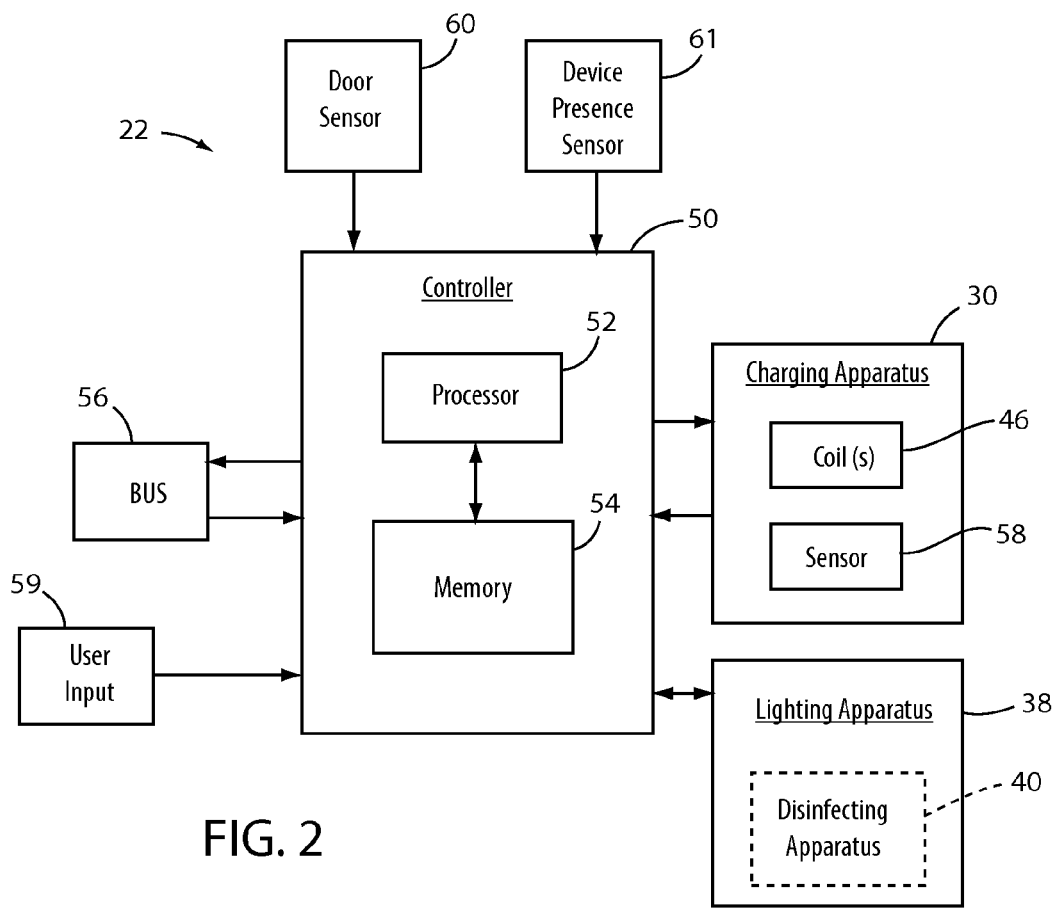
FIG. 2 is a block diagram of a wireless charging and disinfecting system.

Referring now to FIG. 2, a block diagram of the system 22 is shown having control circuitry shown in one embodiment as a controller 50 including a processor 52 and memory 54. The controller 50 may include other or additional analog and/or digital circuitry. The controller 50 may process input information from memory and generate an output to the charging apparatus 30. The charging apparatus may correspond to an inductive charger having inductive coil(s) 46 configured to wirelessly transfer electrical energy for the purposes of charging one or more rechargeable batteries provided in the device 26.

The controller 50 may be configured to receive various inputs from the vehicle via a communication bus 56 and each of the charging apparatus 30, lighting apparatus 38 and the disinfecting apparatus 40. In some embodiments, the inputs may include: 1) a signal indicative of a charging status of the device 26 (e.g. fully charged, partially charged, or low charging state/fully discharged), 2) information from a vehicle connectivity system via a vehicle bus 56 related to at least one determination of a current charging status of device 26 detected via wireless technology or a Universal Serial Bus (USB) port of the vehicle connectivity connectively, 3) a feedback signal from the lighting apparatus 38 and the disinfecting system 40 identifying a disinfecting status and/or light source functionality. The information sent from the vehicle connectivity system may also include a request to controller 50 to determine if device 26 on wireless charging apparatus 30 is charging and a request for the charging status of the device being charged. In some embodiments, the controller 50 may be configured to periodically broadcast a message indicating the charging status of the device 26 to the vehicle connectivity system. In this way, the controller may control the lighting apparatus 38 to illuminate to indicate a charging status of the device 26.

In some embodiments, the charging apparatus 30 may comprise a sensor 58 configured to sense a presence or absence of receivers of the device 26. The sensor 58 may be configured to detect a presence of the device 26 in a transmitter area of the wireless charging apparatus 30. The sensor 58 may also measure the stored charging status of the battery within device 26. The device 26 may be configured to transmit information indicating the stored charging status and the system 30 may be configured to receive a signal from device 26 indicative of a charging status of device 26. The transmitted information may indicate that the device 26 is fully charged, partially charged or at a low charging state/fully discharged. In some embodiments, an in-vehicle connectivity system may be enabled with a wireless communication protocol and may synchronize with the device 26 enabled with the same protocol. Examples of wireless communication protocols that may be used by a chargeable device and compatible with vehicle connectivity system include Bluetooth, infrared, 2-way UHF key fobs, and IEEE 802.11 technologies. In such cases, the charging status information of the device 26 may be communicated directly to and from device 26 to a vehicle connectivity system without requiring sensing of the charging status of device 26 by system 30.

In addition, the controller 50 may utilize the sensor 58 to measure if the device 26 is capable of charging due to misalignment or incompatibility. Detection of misalignment or incompatibility may be achieved by configuring the sensor 58 to measure the amount of power that is being transferred to the device 26 by the system 30. Such measured power information may then be sent to controller 50, which may process the information. The controller 50 may determine an amount of deviation in the measured power relative to a predetermined value or range of values stored in memory 44 to identify if the device is misaligned and/or compatible with the charging apparatus 30. In some embodiments, the controller 50 may be configured to control the lighting apparatus 38 to output a color of light that may be emitted as a pattern to notify an occupant that the device 26 is misaligned.

If the calculated deviation is beyond one or more predetermined threshold values or range of values, the device 26 may be considered significantly misaligned or incompatible with the charging apparatus 30. In addition to information pertaining to the charging statuses of the device battery detected by controller 50 and the detected misalignment of device 26, other information pertaining to the device 26, such as a malfunction of charging apparatus 30 may be detected by controller 50 and communicated via the vehicle bus 56 to the vehicle connectivity system via the bus 56. The controller 50 may also control the lighting apparatus to emit light from at least the first light source to identify a compatibility issue and/or a malfunction of the device 26 or the system 22.

The system 22 may further comprise at least one user input 59 in communication with the controller 50. The user input 59 may be configured to initiate a disinfecting function of the disinfecting apparatus 40. In response to receiving a signal from the user input 59, the controller 50 may activate the second light source of the disinfecting apparatus 40 to sterilize and sanitize an outer surface of the device 26. The controller 50 may be configured to maintain the activation of the second light source to emit the second emission for a predetermined period of time that may correspond to a disinfection period. The second emission may also cause the second photoluminescent portion to become illuminated. In this way, the system 22 may be configured to identify and warn an occupant of the vehicle 10 that a disinfecting function is being processed in the tray 20.

In some embodiments, the system 22 may further comprise a door sensor 60 and a device presence sensor 61 in communication with the controller 50. The door sensor 60 may comprise a switch, for example a magnetic proximity switch, located proximate a closure surface corresponding to the access door 42 and the tray 20. The door sensor 60 may be configured to output a signal to the controller 50 in response to the access door 42 being arranged in a closed position such that a magnet disposed on the access door 42 is located proximate the proximity switch. In this way, the controller 50 may control the second light source such that the ultraviolet light corresponding to the second emission is only output when the access door 42 is arranged in a closed position.

The presence sensor 61 may be disposed in the tray 20 and operable to identify the presence of the device 26. The presence sensor 61 may comprise a capacitive sensor, reflective sensor, light sensor, or any other form of sensor operable to detect the presence of the device 26 in the cavity 120. In response to the device 26 being located in the cavity 120, the presence sensor 61 may send a signal to the controller 50. In response to receiving the signal from the presence sensor 61, the controller 50 may determine if a device is located in the tray 20 such that a disinfecting operation may be activated. For example, in some embodiments, the controller 50 may be configured to only activate a disinfecting operation of the disinfecting apparatus 40 in response receiving a signal that the presence sensor 61 has detected the device 26 in the tray 20.

Figure 3:
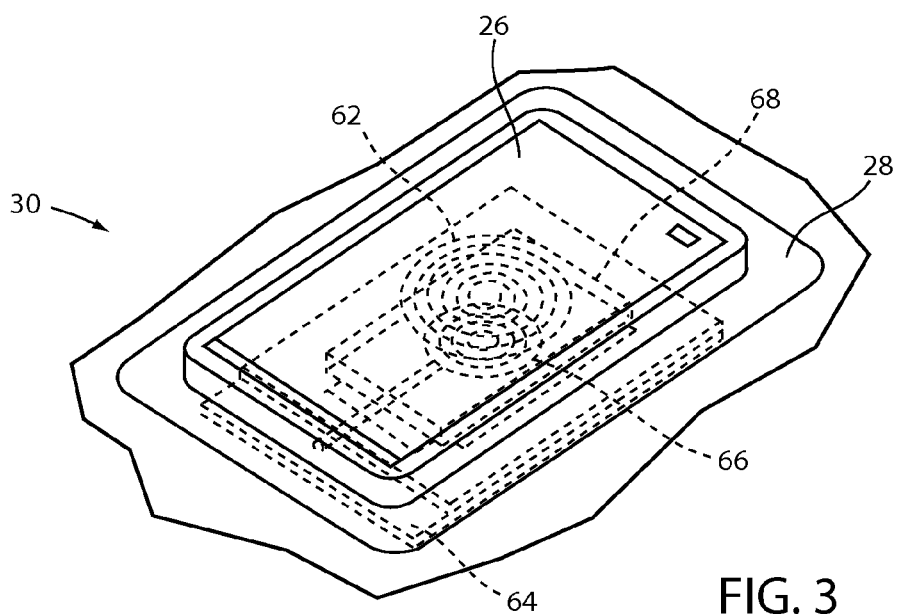
FIG. 3 is a detailed perspective view of a wireless charging apparatus.

Referring to FIG. 3, a detailed perspective view of the charging apparatus 30 is shown demonstrating the charging region 28 relative to a device receiver coil 62 of the device 26. A transmitter section 64 may be housed in the charging apparatus 30. The transmitter section 64 may contain one or more transmitter coils 66 coupled to a connector that is plugged into an external power source of the vehicle 10. A receiver 68 may be housed in device 26. The transmitter section 64 may provide power to the receiver 68 such that the receiver 68 is operable to provide power to a rechargeable battery of the device 26. The transmitter section 64 may also be configured to receive various signals from the device 26. The signals from the device may comprise additional control information that may be received by the transmitter section 64 and communicated to the controller 50 to identify a charge level of the device 26 and adapt to a particular power transfer method to charge the device 26.

Figure 4A:
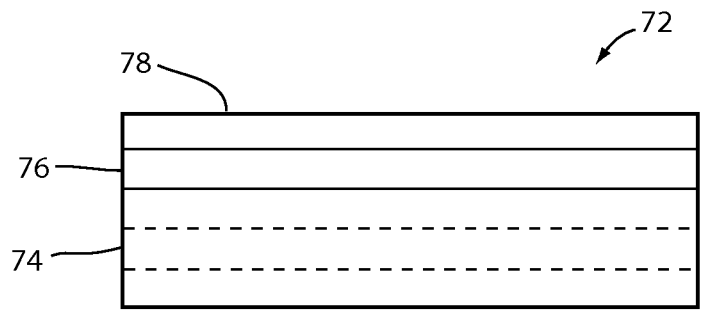
FIG. 4A is a side view of a photoluminescent structure rendered as a coating.
Figure 4B:
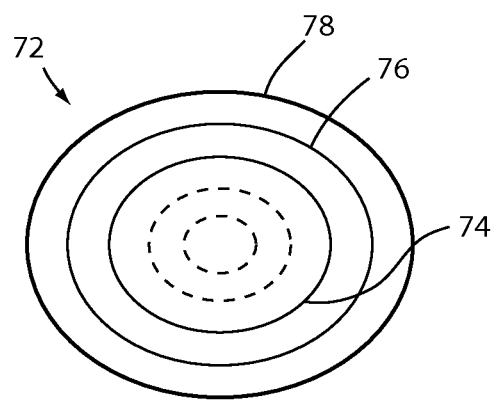
FIG. 4B is a top view of a photoluminescent structure rendered as a discrete particle.
Figure 4C:
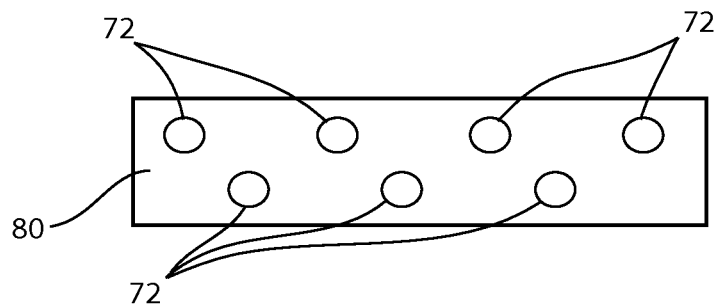
FIG. 4C is a side view of a plurality photoluminescent structures rendered as discrete particles and incorporated into a separate structure.

Referring now to FIGS. 4A, 4B, and 4C, one or more photoluminescent portions of the lighting apparatus 38 and the disinfecting apparatus are discussed to demonstrate a variety of lighting configurations of the system 22. FIGS. 4A-4C demonstrate various embodiments of a photoluminescent structure 72 as a coating (e.g. a film) capable of being applied to a vehicle fixture, a discrete particle capable of being implanted in a vehicle fixture, and a plurality of discrete particles incorporated into a separate structure capable of being applied to a vehicle fixture, respectively. The term fixture as discussed herein may correspond to one or more surfaces or portions of the vehicle 10 proximate the system 22, for example an interior wall of the tray 20. The photoluminescent structure 72 may correspond to the photoluminescent portions as discussed herein, for example the first photoluminescent portion and the second photoluminescent portion. At the most basic level, the photoluminescent structure 72 includes an energy conversion layer 74 that may be provided as a single layer or a multilayer structure, as shown through broken lines in FIGS. 4A and 4B.

The energy conversion layer 74 may include one or more photoluminescent materials having energy converting elements selected from a phosphorescent or a fluorescent material. Some examples of photoluminescent materials may include rylene dyes, terrylene, quarterrylene and phosphorescent pigments, for example zinc sulfide and strontium aluminate. The photoluminescent materials may be formulated to convert an inputted electromagnetic radiation into an outputted electromagnetic radiation generally having a longer wavelength and expressing a color that is not characteristic of the inputted electromagnetic radiation. The difference in wavelength between the inputted and outputted electromagnetic radiations is referred to as the Stokes shift and serves as the principle driving mechanism for an energy conversion process corresponding to a change in wavelength of light, often referred to as down conversion. In the various embodiments discussed herein, each of the wavelengths of light (e.g. the first wavelength, etc.) correspond to electromagnetic radiation utilized in the conversion process.

Each of the photoluminescent portions may comprise at least one photoluminescent structure 72 comprising an energy conversion layer (e.g. conversion layer 74). The energy conversion layer 74 may be prepared by dispersing the photoluminescent material in a polymer matrix 80 to form a homogenous mixture using a variety of methods. Such methods may include preparing the energy conversion layer 74 from a formulation in a liquid carrier medium and coating the energy conversion layer 74 to a desired planar and/or non-planar substrate of a vehicle fixture. The energy conversion layer 74 coating may be deposited on a vehicle fixture by painting, screen-printing, spraying, slot coating, dip coating, roller coating, and bar coating. Additionally, the energy conversion layer 74 may be prepared by methods that do not use a liquid carrier medium.

For example, a solid state solution (homogenous mixture in a dry state) of one or more photoluminescent materials may be incorporated in a polymer matrix 80 to provide the energy conversion layer 74. The polymer matrix 80 may be formed by extrusion, injection molding, compression molding, calendaring, thermoforming, etc. In instances where one or more energy conversion layers 74 are rendered as particles, the single or multilayered energy conversion layers 74 may be implanted into a vehicle fixture or panel. When the energy conversion layer 74 includes a multilayer formulation, each layer may be sequentially coated. Additionally, the layers can be separately prepared and later laminated or embossed together to form an integral layer. The layers may also be coextruded to prepare an integrated multilayered energy conversion structure.

Referring back to FIGS. 4A and 4B, the photoluminescent structure 72 may optionally include at least one stability layer 76 to protect the photoluminescent material contained within the energy conversion layer 74 from photolytic and thermal degradation. The stability layer 76 may be configured as a separate layer optically coupled and adhered to the energy conversion layer 74. The stability layer 76 may also be integrated with the energy conversion layer 74. The photoluminescent structure 72 may also optionally include a protection layer 78 optically coupled and adhered to the stability layer 76 or any layer or coating to protect the photoluminescent structure 72 from physical and chemical damage arising from environmental exposure.

The stability layer 76 and/or the protective layer 78 may be combined with the energy conversion layer 74 to form an integrated photoluminescent structure 72 through sequential coating or printing of each layer, or by sequential lamination or embossing. Alternatively, several layers may be combined by sequential coating, lamination, or embossing to form a substructure. The substructure may then be laminated or embossed to form the integrated photoluminescent structure 72. Once formed, the photoluminescent structure 72 may be applied to a chosen vehicle fixture.

In some embodiments, the photoluminescent structure 72 may be incorporated into a vehicle fixture as one or more discrete multilayered particles as shown in FIG. 2C. The photoluminescent structure 72 may also be provided as one or more discrete multilayered particles dispersed in a polymer matrix 80 that is subsequently applied to a vehicle fixture or panel as a contiguous structure. Additional information regarding the construction of photoluminescent structures to be utilized in at least one photoluminescent portion of a vehicle is disclosed in U.S. Pat. No. 8,232,533 to Kingsley et al., entitled "PHOTOLYTICALLY AND ENVIRONMENTALLY STABLE MULTILAYER STRUCTURE FOR HIGH EFFICIENCY ELECTROMAGNETIC ENERGY CONVERSION AND SUSTAINED SECONDARY EMISSION," filed Jul. 31, 2012, the entire disclosure of which is incorporated herein by reference.

Referring to FIG. 5, a schematic diagram of the lighting apparatus 38 is generally shown according to a front-lit configuration 92. In this configuration, the light or a first emission 94 emitted from the first light source 96 is converted to a third emission 98 by the energy conversion layer 74. The first emission 94 comprises a first wavelength $\lambda_1$, and the third emission 98 comprises a third wavelength. The lighting apparatus 38 comprises the photoluminescent structure 72 disposed on or in at least one photoluminescent portion. In this particular example, the at least one photoluminescent portion is described in reference to the first photoluminescent portion 102. The photoluminescent structure 72 may be rendered as a coating and applied to a substrate 104 of a vehicle fixture, for example an interior wall, panel, fixture, and/or door of the tray 20. The photoluminescent material may also be dispersed as a polymer matrix 80 corresponding to the energy conversion layer 74.

Though the example of FIG. 5 are discussed in reference to the first light source 96 and the first photoluminescent portion 102, similar embodiments may be utilized for the second light source of the disinfecting apparatus 40. The second light source and the second photoluminescent portion are discussed in reference to FIG. 6. Additionally, an example describing a particular implementation of the first light source 96 and the second light source 116 is discussed in reference to FIGS. 7, 8A, and 8B. In general, the first light source 96 may be configured to emit the first emission in the visible light range, and the second light source 116 may be configured to emit the second emission 114 in the ultraviolet color range. In this configuration, the first light source 96 may attribute to an output color of light emitted from the tray 20, wherein the second emission 114 from the second light source 116 may be significantly invisible to the human eye.

In some embodiments, the energy conversion layer 74 may further include the stability layer 76 and/or protective layer 78. In response to the first light source 96 being activated, the first emission 94 is received by the energy conversion layer 74 and converted from the first emission 94 having the first wavelength $\lambda_1$ to the third emission 98 having at least the third wavelength. The third emission 98 may comprise a plurality of wavelengths configured to emit a variety of colors of light from the first photoluminescent portion 102.

In various embodiments, the lighting apparatus 38 comprises at least one photoluminescent material incorporated in the polymer matrix 80 and/or energy conversion layer 74 and is configured to convert the first emission 94 at the first wavelength $\lambda_1$ to the third emission 98 having at least the third wavelength. In order to generate the plurality of wavelengths, the energy conversion layer 74 may comprise one or more photoluminescent materials configured to emit the third emission 98 as wavelengths of light in the red, green, and/or blue color spectrums. Such photoluminescent materials may further be combined to generate a wide variety of colors of light for the third emission 98. For example, the red, green, and blue-emitting photoluminescent materials may be utilized in a variety of proportions and combinations to control the output color of the third emission 98.

Each of the photoluminescent materials may vary in output intensity, output wavelength, and peak absorption wavelengths based on a particular photochemical structure and combinations of photochemical structures utilized in the energy conversion layer 74. As an example, the third emission 98 may be changed by adjusting the wavelength of the first emission $\lambda_1$ to activate the photoluminescent materials at different intensities to alter the color of the third emission 98. In addition to, or alternatively to the red, green, and blue-emitting photoluminescent materials, other photoluminescent materials may be utilized alone and in various combinations to generate the third emission 98 in a wide variety of colors. In this way, the lighting apparatus 38 may be configured for a variety of applications to provide a desired lighting color and effect for a vehicle.

To achieve the various colors and combinations of photoluminescent materials described herein, the lighting apparatus 38 may utilize any form of photoluminescent materials, for example phospholuminescent materials, organic and inorganic dyes, etc. For additional information regarding fabrication and utilization of photoluminescent materials to achieve various emissions, refer to U.S. Pat. No. 8,207,511 to Bortz et al., entitled "PHOTOLUMINESCENT FIBERS, COMPOSITIONS AND FABRICS MADE THEREFROM," filed Jun. 26, 2012; U.S. Pat. No. 8,247,761 to Agrawal et al., entitled "PHOTOLUMINESCENT MARKINGS WITH FUNCTIONAL OVERLAYERS," filed Aug. 21, 2012; U.S. Pat. No. 8,519,359B2 to Kingsley et al., entitled "PHOTOLYTICALLY AND ENVIRONMENTALLY STABLE MULTILAYER STRUCTURE FOR HIGH EFFICIENCY ELECTROMAGNETIC ENERGY CONVERSION AND SUSTAINED SECONDARY EMISSION," filed Aug. 27, 2013; U.S. Pat. No. 8,664,624B2 to Kingsley et al., entitled "ILLUMINATION DELIVERY SYSTEM FOR GENERATING SUSTAINED SECONDARY EMISSION," filed Mar. 4, 2014; U.S. Patent Publication No. 2012/0183677 to Agrawal et al., entitled "PHOTOLUMINESCENT COMPOSITIONS, METHODS OF MANUFACTURE AND NOVEL USES," filed Jul. 19, 2012; U.S. Patent Publication No. 2014/0065442A1 to Kingsley et al., entitled "PHOTOLUMINESCENT OBJECTS," filed Mar. 6, 2014; and U.S. Patent Publication No. 2014/0103258A1 to Agrawal et al., entitled "CHROMIC LUMINESCENT COMPOSITIONS AND TEXTILES," filed Apr. 17, 2014, all of which are hereby incorporated herein by reference in their entirety.

The first light source 96 may also be referred to as an excitation source and is operable to emit at least the first emission 94. The first light source 96 may comprise any form of light source, for example halogen lighting, fluorescent lighting, light emitting diodes (LEDs), organic LEDs (OLEDs), polymer LEDs (PLEDs), solid state lighting or any other form of lighting configured to output the first emission 94. The first emission 94 from the first light source 96 may be configured such that the first wavelength $\lambda_1$ corresponds to at least one absorption wavelength of the one or more photoluminescent materials of the energy conversion layer 74 and/or polymer matrix 80. In response to receiving the light at the first wavelength $\lambda_1$, the energy conversion layer 74 may be excited and output the one or more output wavelengths. The first emission 94 provides an excitation source for the energy conversion layer 74 by targeting absorption wavelengths of a particular photoluminescent material or combination thereof utilized therein. As such, the lighting apparatus 38 may configured to output the third emission 98 to generate a desired light intensity and color.

In an exemplary implementation, the first light source 96 comprises an LED configured to emit the first wavelength $\lambda_1$ which may correspond to a blue spectral, violet, and/or ultraviolet color range. The blue spectral color range comprises a range of wavelengths generally expressed as blue light (~440-500 nm). In some embodiments, the first wavelength $\lambda_1$ may comprise a wavelength in the ultraviolet and near ultraviolet color range (~100-450 nm) and correspond to a longer wavelength than the second wavelength. In an exemplary implementation, $\lambda_1$ may be approximately equal to 470 nm. Though particular wavelengths and ranges of wavelengths are discussed in reference to the first wavelength $\lambda_1$, the first wavelength $\lambda_1$ may generally be configured to excite any photoluminescent material.

In an exemplary implementation, the first wavelength $\lambda_1$ may be approximately less than 500 nm. The blue spectral color range and shorter wavelengths may be utilized as an excitation source for the lighting apparatus 38 due to these wavelengths having limited perceptual acuity in the visible spectrum of the human eye. By utilizing shorter wavelengths for the first wavelength $\lambda_1$, and converting the first wavelength with the conversion layer 74 to at least one longer wavelength, the lighting apparatus 38 creates a visual effect of light originating from the photoluminescent structure 72.

As discussed herein, the second emission may be emitted from the second light source which may correspond to the ultraviolet light source. The second light source may be configured to emit the second emission corresponding to a wavelength in the ultraviolet light range of approximately 10 nm to 400 nm. The second light source may comprise any combination of one or more ultraviolet radiation emitters. For example, the ultraviolet light source may include a high intensity ultraviolet lamp (e.g., a high intensity mercury lamp), an ultraviolet light emitting diode (LED), super luminescent LEDs, laser diodes, and/or the like. In some embodiments, the second light source may include a set of light emitting diodes manufactured with one or more layers of materials selected from the group-Ill nitride material system (e.g., AlxInyGai_x_YN, where 0<x, y<1, and x+y<1 and/or alloys thereof). In an illustrative embodiment, the second light source may be configured to emit ultraviolet radiation in the range of approximately 10 nm to 400 nm and in some embodiments may emit radiation at approximately 200 nm to 300 nm.

As discussed herein, each of the plurality of wavelengths corresponding to the third emission 98 and the fourth emission (i.e. the output emissions) may correspond to significantly different spectral color ranges. The plurality of wavelengths may be generated by a red-emitting photoluminescent material having a wavelength of approximately 620-750 nm, a green emitting photoluminescent material having a wavelength of approximately 526-606 nm, and a blue or blue green emitting photoluminescent material having a wavelength longer than the first wavelength $\lambda_1$ and approximately 430-525 nm in one embodiment. The plurality of wavelengths may be utilized to generate a wide variety of colors of light from the each of the photoluminescent portions (e.g. the first photoluminescent portion and the second photoluminescent portion) converted from the first wavelength $\lambda_1$. The fourth emission may similarly utilize photoluminescent materials to output a color of light different from the first emission 94 and the third emission 98.

Referring to FIG. 6, the lighting apparatus 38 is generally shown according to a back-lit configuration 110. Similar to the front-lit configuration 92, the back-lit configuration 110 comprises an energy conversion layer 74 and/or photoluminescent material dispersed in a polymer matrix 80. As shown in FIG. 6, the lighting apparatus 38 may be configured to convert the second emission 114 from the second light source 116 to the fourth emission 118. In this configuration, the lighting apparatus 38 may be configured to emit the second emission 114 into a cavity 120 formed by the tray 20. The second emission 114 may pass through a volume of the cavity 120 and be received by the material of the tray 20 and the access door 42. As discussed herein, the access door 42 and the tray 20 may be composed of material configured to absorb and/or reflect ultraviolet radiation comprising wavelengths approximately less than 400 nm. In this way, one or more passengers in the passenger compartment 8 may be protected from the possibly harmful ultraviolet radiation.

In order to provide a visible notification of the status output by the first light source 96 and/or the second light source 116 of the lighting apparatus 38, the access door 42 may be configured to pass light in the visible range while blocking ultraviolet radiation. That is, the light corresponding to the third emission 98 and/or the fourth emission 188 may be output through the access door 42 to provide a visible notification of a state of the system 22. In this way, the third emission 98 emitted from the first photoluminescent portion 102 and/or the fourth emission 118 emitted from the second photoluminescent portion 112 may be output through the access door 42 such that the color of the light emitted is visible to an occupant of the vehicle 10.

In a particular example, the second photoluminescent portion 112 may be disposed on an interior surface 124 of the access door 42. In this configuration, the second emission 114, comprising the ultraviolet light emitted from the second light source 116, may be converted by the second photoluminescent portion 112 to emit the fourth emission 118. Any ultraviolet light that is not converted by the second photoluminescent portion may be absorbed and/or reflected back into the cavity 120. The fourth emission 118 may correspond to light in the visible range comprising one or more wavelengths approximately greater than 400 nm. As such, the filtering properties of the materials and or coatings applied to and/or disposed in the material of the access door 42 may allow the fourth emission 118 to pass outward through the access door 42 such that the door glows and emits a color of light corresponding to the fourth emission 118.

Though the second photoluminescent portion 112 is discussed in reference to FIG. 6, the system 22 may provide similar lighting effects in embodiments comprising the first photoluminescent portion 102 and/or the second photo luminescent portion 112 disposed on any of the interior surfaces of the charging and disinfecting compartment 43. For example, each of the photoluminescent portions 102 and 112 may be disposed on one or more of the interior surfaces of the access door 42, the tray 20, the charging region 28 or any other surface within the cavity 120 formed by the tray 20 and the access door 42. In the various embodiments discussed herein, the system 22 may be operable to provide a visual notification of the charging state and/or disinfection status of the device 26.

Figure 7:
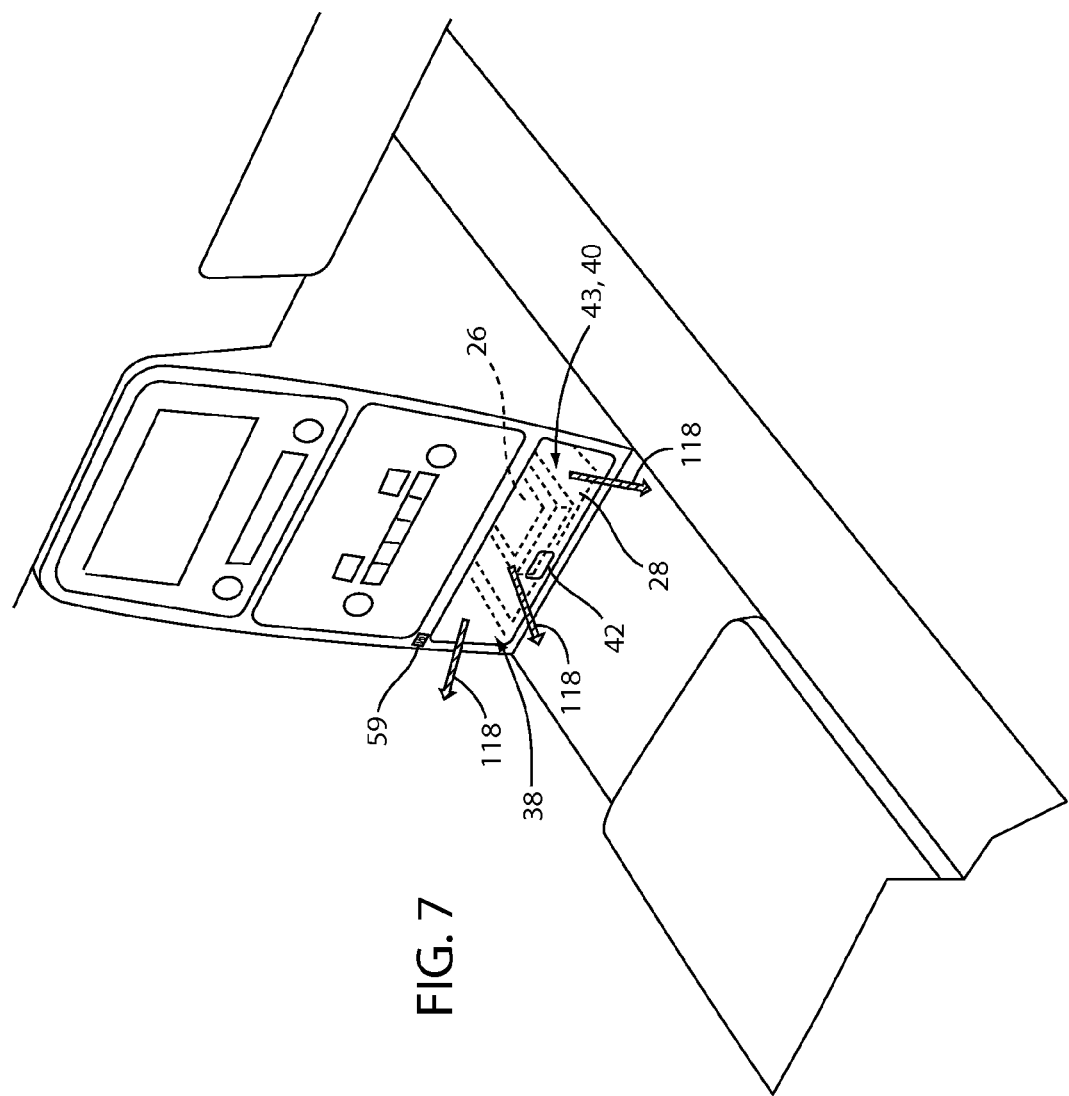
FIG. 7 is a perspective view a wireless charging and disinfecting system.

Referring now to FIG. 7, the system 22 is shown in a disinfecting mode. In this configuration, the controller 50 may be configured to control the lighting apparatus 38 and a disinfecting apparatus 40 in response to a signal received from the user input 59. The access door 42 is shown enclosing the charging and disinfecting compartment 43. The device 26 is shown resting on a surface corresponding to the charging region 28. In response to the device 26 being partially charged, and the disinfecting apparatus 40 being configured in a disinfecting mode, the system 22 may be configured to output at least the fourth emission 118.

As discussed herein, the controller 50 may be operable to control the second light source 116 to emit the second emission 114. In response receiving the second emission 114, the second photoluminescent portion 112 may become excited and output the fourth emission 118. The fourth emission 118 may correspond to a color of light in the visible color range. In this configuration, the fourth emission 118 may be transmitted through the material of the access door 42 such that the fourth emission 118 is visible from the passenger compartment 8 of the vehicle 10. In this way, the system 22 may be configured to provide a visual alert to an occupant of the vehicle 10 that the disinfecting apparatus 40 is actively emitting ultraviolet radiation.

In some implementations, each of the photoluminescent portions 102 and 112 may be disposed on an interior surface of the access door 42. In this configuration, each of the photoluminescent portions 102 and 112 may be selectively illuminated to generate an ambient glow from the access door 42 in response to receiving the first emission 94 and the second emission 114, respectively. The access door may further comprise shielding that may prevent electromagnetic interference (EMI) from entering the passenger compartment 8. The shielding may correspond to a transparent EMI shielding film, foil, or glass. For example, the shielding may correspond to a polymeric material with an electrically conductive coating configured to limit the passage of EMI through the access door 42.

Figure 8A:
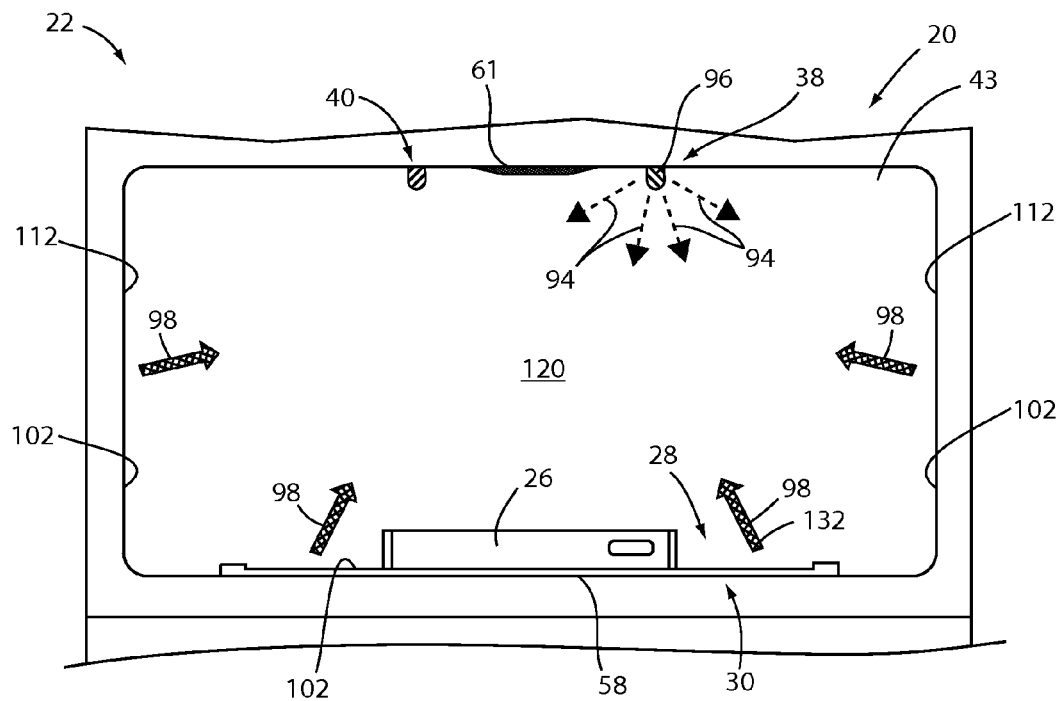
FIG. 8A is a front detailed view of a wireless charging and disinfecting system in a first state.

Referring now FIGS. 8A and 8B, the charging and disinfecting compartment 43 of the system 22 will be described in reference to a variety of charging status and disinfecting modes. Referring to FIG. 8A, the lighting apparatus 38 is shown having the first light source 96 activated. The first photoluminescent portion 102 may be disposed on an inner surface of the disinfecting compartment 43 and/or the access door 42. In response to the first light source 96 emitting the first emission 94, the first photoluminescent portion 102 may become excited and emit the third emission 98. As described herein, the third emission 98 may correspond to a wide range of colors of light that may be controlled by utilizing one or more photoluminescent materials in the energy conversion layer 74. In this configuration, the system 22 may be configured to emit light in a first color 132 corresponding to the one or more wavelengths of the third emission 98. The first color 132 of light may be emitted outward from the compartment 43 through the access door 42.

The second photoluminescent portion 112 may similarly be disposed on an inner surface of the disinfecting compartment 43 and/or the access door 42. In response to the second light source 116 emitting the second emission 114, the second photoluminescent portion 112 may become excited and emit the fourth emission 118. As described herein, the fourth emission 118 may correspond to a wide range of colors of light that may be controlled by utilizing one or more photoluminescent materials in the energy conversion layer 74. In this configuration, the system 22 may be configured to emit light in a second color 134 corresponding to the one or more wavelengths of the fourth emission 118. The second color of light may be emitted outward through the access door 42.

In some embodiments, the system 22 may be operable to blend the first color 132 and the second color 134 in response to a charging and/or disinfecting status of the system 22. For example, in some embodiments, the first photoluminescent portion 102 may be configured to emit the third emission 98 in the first color 132, which may correspond to a green color having a wavelength of approximately 520 nm to 560 nm. In this configuration, the color of light output through the access door 42 may be substantially green in response to the system processing a charging function.

The second photoluminescent portion 112 may be configured to emit the fourth emission 118 having the second color 134 corresponding to a red color having a wavelength of approximately 620 nm to 750 nm. In this configuration, the color of light output through the access door 42 may be substantially red in response to the system processing a disinfecting function. Additionally, the system may be operable to process a charging function and a disinfecting function at the same time. In this configuration, the third emission 98 and the fourth emission 118 may be activated together to output a light in a combination of the first color 132 and the second color 134 to output a yellow color of light through the access door 42. Though specific colors of light are discussed in reference to the exemplary embodiments disclosed herein, the first photoluminescent portion 102 and the second photoluminescent portion 112 may be configured to emit a variety of colors of light.

The controller 50 may further be configured to adjust the color of the light output through the access door 42 by adjusting the intensity and light energy emitted from the first light source 96 while the second light source 116 is active. For example, during a disinfecting function, the second light source 116 may be active such that the second emission 114 excites the second photoluminescent portion 112 to output the fourth emission 118. Additionally, the controller 50 may activate the first light source 96 at a range of intensities. In this way, the system 22 may be operable to vary the output color of light emitted through the access door 42. In this configuration, the controller 50 may be operable to selectively blend the first color 132 and the second color 134 to vary the output color of light emitted through the access door 42 from a substantially red color to a substantially yellow color. The output color of light emitted through the access door 42 may correspond to a charge level of the electronic device 26.

Though the output color emitted from the tray 20 corresponding to the charging and disinfecting compartment 43 is described herein as being emitted through the access door 42, it may be understood that the system 22 may similarly output a color corresponding to a charging status of the device 26 by projecting ambient light from the cavity 120. As discussed herein, the first photoluminescent portion 102 may be disposed on and/or dispersed in any of the interior surfaces defining a cavity 120. In this way, the system 22 may be operable to control the color of light output from the tray 20 through the cavity 120 similar to the process described in reference to the access door 42. As such, the system 22 may be operable to control the color of the light output from the tray 20 while the access door 42 is open or in some embodiments that may not require the ultraviolet absorbing properties of the access door 42.

Figure 8B:
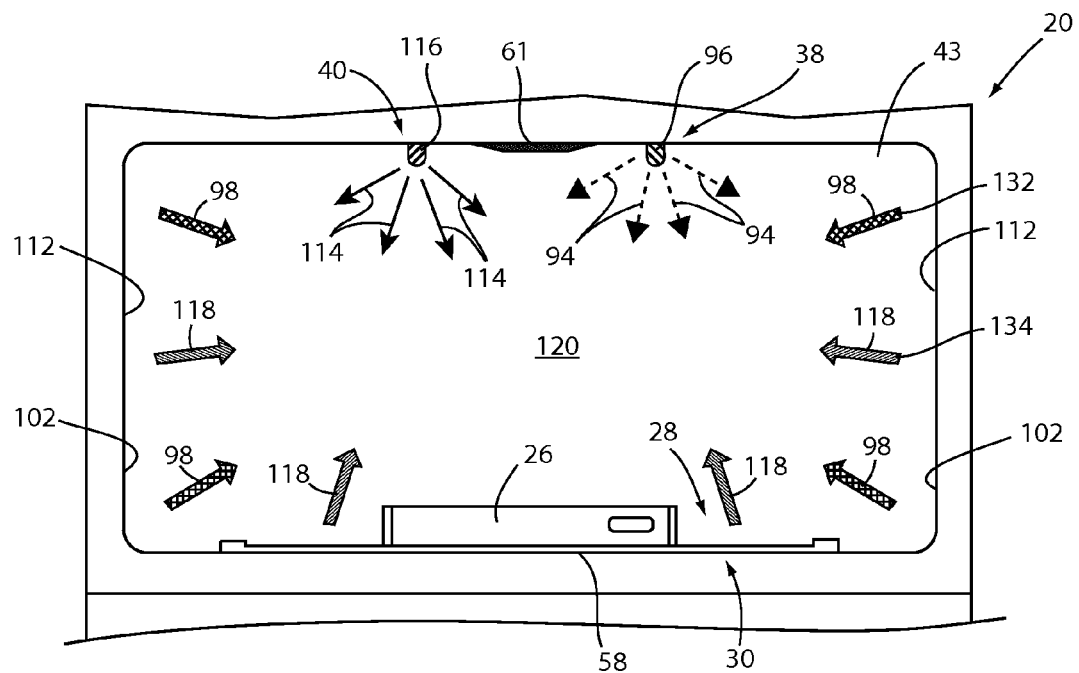
FIG. 8B is a front detailed view of a wireless charging and disinfecting system in a first state in accordance with the disclosure.

Referring to FIG. 8B, the lighting apparatus 38 including the disinfecting apparatus 40 is shown having the first light source 96 and the second light source 116 activated. As discussed in reference to FIGS. 7 and 8A, the controller 50 may be operable to control the first light source 96 to generate a range of colors by blending the first emission 94 with the third emission 98. Each of the first photoluminescent portion 102 and the second photoluminescent portion 112 may be disposed proximate one or more of the interior surfaces of the access door 42, the tray 20, the charging region 28 or any other surface within the cavity 120 formed by the tray 20 and the access door 42. In this configuration, the controller 50 may be operable to control the second light source 116 to generate at least one color output from the second photoluminescent portion 112. Further, the system 22 may be operable to selectively activate the first light source 96 and/or the second light source 116 to selectively combine the output colors of the first light source 96, the first photoluminescent portion 102, and the second photoluminescent portion 112. The second emission 114 from the second light source 116 may not significantly alter the color of light emitted from the tray 20 due to the ultraviolet light being outside the visible color range.

As described herein, the system 22 may be operable to generate a variety of colors by combining colors of light generated by the first light source 96, the first photoluminescent portion 102, and the second photoluminescent portion 112. In order to facilitate such selective color blending and activation, the first photoluminescent portion 102 may comprise a first absorption range corresponding to the first emission, which may range from approximately 420 nm to 500 nm. Additionally, the second photoluminescent portion 112 may comprise a second absorption range corresponding to the second emission 114, which may range from approximately 200 nm to 400 nm. In this configuration, the controller 50 may be configured to selectively activate the third emission 98 and the fourth emission 118 independently. As such, the system may be operable to output a wide variety of colors of light by selectively activating the first light source 96 and the second light source 116.

The disclosure provides for a system operable to control a charging and disinfection process in a vehicle. The system comprises a lighting apparatus that incorporates a disinfecting apparatus configured to output a color of light from a tray, console, or any other opening or cavity of a vehicle. The color of light may be controlled by a controller of the system to notify an occupant of the vehicle of at least one of a charging status and a disinfection process status. As such, the disclosure provides for a versatile and cost effective system that may be operable to wirelessly charge an electronic device, safely disinfect the electronic device, and provide a visible notification to an occupant of a vehicle corresponding the charging and/or disinfection process.

As discussed herein, the terms first, second, third, etc. may provide designations in reference to the figures for clarity. For example, a first wavelength may correspond to an excitation emission and a third wavelength may correspond to a corresponding output emission from a photoluminescent portion. Such designations may serve to demonstrate exemplary arrangements and compositions and should not be considered to designate a specific number of elements or essential components of any specific implementation of the disclosure, unless clearly specified otherwise. Further, the specific numeric designations in the specification may not correspond to similar numeric designations in the claims. For example, the terms first, second, third, etc. may refer to an order of introduction of elements in the claims and should not be limited to a specific numeric designation as described in the specification.

It is to be understood that variations and modifications can be made on the aforementioned structure without departing from the concepts of the present invention, and further it is to be understood that such concepts are intended to be covered by the following claims unless these claims by their language expressly state otherwise.

What is claimed is:

1. A charging and disinfecting tray for a vehicle comprising:
   a wireless charger for charging an electronic device on the tray;
   a lighting apparatus comprising a disinfecting apparatus comprising at least one photoluminescent indicator; and
   a controller configured to control the wireless charger and the lighting apparatus and operable to activate the at least one photoluminescent indicator by initiating a sterilization operation with the disinfecting apparatus.

2. The charging and disinfecting tray according to claim 1, wherein the disinfecting apparatus comprises an ultraviolet light source configured to illuminate a first photoluminescent portion of the at least one photoluminescent indicator in a first color.

3. The charging and disinfecting tray according to claim 2, wherein the lighting apparatus further comprises a visible light source configured to provide ambient lighting for the tray.

4. The charging and disinfecting tray according to claim 3, wherein the visible light source is configured to illuminate a second photoluminescent portion of the at least one photoluminescent indicator in a second color different than the first color.

5. The charging and disinfecting tray according to claim 4, wherein the first photoluminescent portion comprises a first absorption range corresponding to the visible light source and the second photoluminescent portion comprises a second absorption range corresponding to the ultraviolet light source.

6. The charging and disinfecting tray according to claim 4, wherein the visible light source is configured to emit an emission having a third color different from the first color and the second color.

7. The charging and disinfecting tray according to claim 6, wherein the controller is further configured to control an intensity of the emission from the visible light source to control an output color of light emitted from the tray.

8. The charging and disinfecting tray according to claim 7, wherein the controller is further configured to adjust the output color of light emitted from the tray by selectively activating the visible light source blend the second color and the third color during the sterilization operation.

9. A charging tray for a vehicle comprising:
   a wireless charger for charging an electronic device on the tray disposed in a disinfecting compartment;
   a lighting apparatus comprising at least one photoluminescent indicator; and
   a controller configured to control the wireless charger and the lighting apparatus and operable to control the lighting apparatus to output a color of light corresponding to a charge level of the electronic device.

10. The charging tray according to claim 9, wherein the lighting apparatus comprises a visible light source configured to excite a first photoluminescent portion of the photoluminescent indicator.

11. The charging tray according to claim 10, wherein the visible light source is configured to emit a first emission corresponding to a first color of light and the photoluminescent portion is configured to emit a second emission corresponding to a second color of light.

12. The charging tray according to claim 11, wherein controller is configured to adjust an intensity of the visible light source to selectively blend the first color with the second color to generate an output color emitted from the compartment.

13. The charging tray according to claim 12, wherein the output color emitted from the compartment corresponds to the charge level of the electronic device.

14. The charging tray according to claim 9, wherein the lighting apparatus further comprises a disinfecting apparatus comprising an ultraviolet light source.

15. The charging tray according to claim 9, wherein the at least one photoluminescent indicator comprises a second photoluminescent portion configured to be selectively excited in response to receiving an emission from the ultraviolet light source.

16. A charging and disinfecting tray for a vehicle comprising:
   a wireless charger for charging an electronic device on the tray;
   a lighting apparatus comprising a disinfecting apparatus comprising at least one photoluminescent indicator; and
   a controller configured to control the wireless charger and the lighting apparatus and operable to activate the photoluminescent indicator by initiating a sterilization operation with the disinfecting apparatus.

17. The charging and disinfecting tray according to claim 16, wherein the lighting apparatus comprises a visible light source operable to emit a first emission corresponding to a first color.

18. The charging and disinfecting tray according to claim 17, wherein first emission is configured to excite a first photoluminescent portion of the photoluminescent indicator to output a second color of light.

19. The charging and disinfecting tray according to claim 18, wherein the disinfecting apparatus is configured to emit an ultraviolet emission of light configured to excite a second photoluminescent portion of the photoluminescent indicator to output a third color of light.

20. The charging and disinfecting tray according to claim 18, wherein the controller is further operable to selectively combine the second color and the third color to generate an output color corresponding to a status of at least one of the wireless charger, the disinfecting apparatus, and the electronic device.

* * * * *